United States Patent
Kotler

[19]

[11] Patent Number: 5,877,825
[45] Date of Patent: Mar. 2, 1999

[54] METHOD AND DEVICE INCLUDING ELECTRO-OPTICAL SHUTTER FOR PROTECTION FROM PULSED RADIATION

[75] Inventor: Zvi Kotler, Tel-Aviv, Israel

[73] Assignee: The State of Israel, Atomic Energy Commission Soreq Nuclear Research Center, Yavne, Israel

[21] Appl. No.: 865,024

[22] Filed: May 29, 1997

[30] Foreign Application Priority Data

May 31, 1996 [IL] Israel .......................................... 118517

[51] Int. Cl.⁶ ................................ G02F 1/13; A61F 9/06; G02C 9/00; B23K 37/00
[52] U.S. Cl. .................................... 349/14; 349/19; 2/432; 219/147
[58] Field of Search .................................. 349/13, 14, 19; 351/41, 44–49, 213; 606/10, 11; 219/130.15, 147, 121.6; 2/63, 15, 905, 909, 433, 432

[56] References Cited

U.S. PATENT DOCUMENTS

| | | | |
|---|---|---|---|
| 4,237,557 | 12/1980 | Gordon | ........................................... 2/8 |
| 4,560,239 | 12/1985 | Katz . | |
| 4,620,322 | 11/1986 | Eggenschwiler et al. | ............... 349/104 |
| 4,728,173 | 3/1988 | Toth | ......................................... 349/101 |
| 5,067,795 | 11/1991 | Senatore | .................................... 351/41 |
| 5,252,817 | 10/1993 | Fergason et al. | ........................ 250/205 |
| 5,276,539 | 1/1994 | Humphrey . | |

*Primary Examiner*—Hung X. Dang
*Assistant Examiner*—Kenneth Parker
*Attorney, Agent, or Firm*—Helfgott & Karas, P.C.

[57] ABSTRACT

A method and a safety device for the protection of a user's eye, or other radiation sensitive system, from a pulsed radiation emitted by a radiation source by means of an electro-optical shutter used in conjunction with the radiation source. The electro-optical sutter defines the field of view of the user or of the system and is capable of being switched by an electrical voltage signal from a transparent state to an opaque state within a response time $\Delta t_r$. The method comprises applying to the electro-optical shutter the electrical voltage signal at an operational time interval $\Delta t_o$, prior to the emission of each radiation pulse and keeping the electro-optical shutter in its opaque state until the radiation pulse is emitted. The operational time interval $\Delta t_o$ is at least slightly longer than the response time $\Delta t_r$ so that, by the time of emission of each radiation pulse, the electro-optical shutter is in its opaque state.

21 Claims, 2 Drawing Sheets

METHOD AND DEVICE INCLUDING ELECTRO-OPTICAL SHUTTER FOR PROTECTION FROM PULSED RADIATION

FIELD OF THE INVENTION

The invention relates to a method and device for the protection of human eyes, or other radiation sensitive systems, from pulsed radiation, particularly from short radiation pulses in a relatively broad range of wavelengths. The invention is specifically useful for the protection from radiation of tunable pulsed lasers.

BACKGROUND OF THE INVENTION

The increased use of tunable pulsed lasers in industrial, medical, and scientific applications requires safety measures to be taken to protect the eyes of users from the laser radiation.

There have been suggested safety glasses which provide a selective blocking of radiation of a specific wavelength. However, these glasses leave relatively broad regions of the spectrum open for vision and consequently are not suitable for the protection from tunable lasers over the entire visible range. Another important disadvantage of glasses of this kind is the chromatic distortion of their field of view.

To enable the eye protection in a broad range of wavelengths, it has been suggested to utilize, in safety glasses, lenses in the form of electro-optical shutters which are switched from their transparent state into their opaque state by an electrical voltage signal applied thereto.

Such safety glasses are disclosed, for example, in U.S. Pat. No. 4,560,239 and U.S. Pat. No. 5,067,795. In the glasses, an optical sensing device identifies a threatening radiation beam and activates power supply means to quickly switch the shutters into their opaque state.

U.S. Pat. No. 5,276,539 discloses safety glasses of the above kind in which the glasses transmittance varies in accordance with the intensity of radiation in their field of view. Thus, the glasses comprise two electro-optical shutters and an optical sensing device which measures the average intensity of radiation in the field of view of the shutters and activates control means to vary transmittance of the glasses by switching the shutters from their transparent to their opaque state at a relatively high frequency and for time intervals which are selectively controlled depending on the measured intensity of radiation. Thereby, the level of brightness of the view perceived by the observer is regulated. As indicated in U.S. Pat. No. 5,276,539, in order to be undetectable by the human eye, the frequency of switching the electro-optical shutters must be not less than a threshold value of 22 Hz.

In all the above disclosures, the electro-optical shutters are liquid-crystal shutters having a sufficiently short response time needed for their switching from a state of high transparency to a state of complete opaqueness and, consequently, capable of passing from one state to another at a relatively high rate. Certain liquid crystal shutters have the additional advantage that they can provide a substantially wide field of view (more than 130°) and can ensure eye protection over practically the entire visible range with minimal chromatic distortion.

However, neither of the devices described above is suitable for the protection from a radiation of pulsed lasers (such as, for example, mode-locked or Q-switched lasers) in which a normal duration of pulses is extremely short, i.e. in the nano- or picosecond range, while the shortest response time which can presently be obtained with liquid crystals is about a few tens of microseconds (ferroelectric liquid crystals), not to mention the response time of conventional liquid crystal shutters which is in the order of milliseconds (supertwisted nematic (STN) or twisted nematic (TN) liquid crystals).

It is therefore the object of the present invention to provide a new method and device for the protection of human eyes, or other radiation sensitive systems, from a pulsed radiation in a relatively broad spectral region.

SUMMARY OF THE INVENTION

In accordance with the present invention there is provided a method for the protection of a user's eye or other radiation sensitive system from a pulsed radiation emitted by a radiation source, by means of an electro-optical shutter used in conjunction with said radiation source and defining the field of view of the user or of the system, the electro-optical shutter being capable of being switched by an electrical voltage signal from a transparent state to an opaque state within a response time $\Delta t_r$; said method comprising:

applying said electrical voltage signal to said electro-optical shutter at an operational time interval $\Delta t_o$ prior to the emission of each radiation pulse, the operational time interval $\Delta t_o$ being at least slightly longer than the response time $\Delta t_r$ so that, by the time of emission of each radiation pulse, the electro-optical shutter is in its opaque state; and keeping said electro-optical shutter in its opaque state until the radiation pulse is emitted.

The method according to the present invention is particularly useful when a duration of radiation pulses is shorter than the response time of the electro-optical shutter. This is most often the case with pulsed lasers. However, the method can also be useful for the protection from any other short radiation pulses or bursts. The latter may be caused, for example, by an interaction of laser radiation with a material during the material processing by the laser.

With the laser emitting each radiation pulse within a delay time $\Delta t_d$ after the laser is triggered, internally or externally, it is preferable that the electro-optical shutter has the response time $\Delta t_r$ shorter than the delay time $\Delta t_d$ which, for example, with Q-switched pulsed lasers is usually more than 100μ. This condition can be achieved by the electro-optical shutter being in the form of a liquid crystal shutter (LCS) and, particularly, a ferroelectric LCS which among presently available liquid crystals has a minimal response time, i.e. in the order of tens of microseconds. In this case, the operational time interval $\Delta t_o$ can equal or even be slightly shorter than the delay time $\Delta t_d$, by virtue of which the shutter can operate at rates of the same order as the laser. It is specifically advantageous that the operational time interval $\Delta t_o$ equals the delay time $\Delta t_d$, whereby the shutter can be triggered simultaneously with the laser, by virtue of which a synchronization of their operating regimes can be essentially simplified. However, even when the shutter and the laser are not triggered simultaneously, i.e. when the operational time interval $\Delta t_o$ does not equal the delay time $\Delta t_d$ of the laser, the method according to the present invention still enables the synchronization of an operating frequency and exposure phase of the electro-optical shutter and a triggering rate and phase of the laser. Thus, the general condition for the synchronization of the operating frequency $f_s$ of the electro-optical shutter with the triggering rate $f_l$ of the laser, according to the present invention is:

$$f_s = n f_l,$$

where n=1, 2, 3, etc.

In order to ensure that the flickering of the electro-optical shutter between its transparent and opaque states is undetectable by the user, the method according to the present invention preferably provides that either the shutter operates at frequencies which are higher than the recovery rate of the eye or the time for which the user's field of view is blocked lasts, irrespective of the operating frequency of the shutter, not longer than a threshold time which is about 300 μs.

Both the above conditions clearly imply the use of fast electro-optical shutters such as the ferroelectric LCSs mentioned above, which can operate at switching frequencies as high as tens of kilohertz and which can provide for a rather short operational time interval. Thus, in addition to the effective protection, the method according to the present invention can provide good vision, there being taken advantage of the fact that, with pulsed lasers, the time for which the user's field of view should be blocked is very short and the triggering rates at which the lasers often operate are relatively high.

It should be mentioned that the method of the present invention can be employed not only for eye protection but also for the protection of radiation sensitive systems, such as, for example, CCD cameras and sensors.

When required, the method according to the present invention can provide for a fail safe operation which is especially important for laser applications and which ensures that the laser is triggered only upon a verification of the fact that the shutter is in its opaque state. The fail safe operation can also include an optical density detection of the shutter, ensuring that the laser is triggered only after the optical density reaches its predetermined value.

In accordance with the present invention there is also provided, for use in conjunction with a radiation source, a safety device for the protection of a user's eyes, or other radiation sensitive systems, from a pulsed radiation emitted by the radiation source, the safety device comprising:

at least one lens defining the field of view of the user, the lens being in the form of an electro-optical shutter capable of being switched by an electrical voltage signal from a transparent state to an opaque state with a response time $\Delta t_r$ therebetween; and control means adapted for applying said electrical voltage signal to said electro-optical shutter at an operational time interval $\Delta t_o$ prior to the emission of a radiation pulse, the operational time interval $\Delta t_o$ being at least slightly longer than the response time $\Delta t_r$ so that, by the time of emission of each radiation pulse, the electro-optical shutter is in its opaque state; and for keeping said electro-optical shutter in its opaque state until the radiation pulse is emitted.

In a preferred embodiment of the present invention, the radiation source is a pulsed laser. In this case, the electro-optical shutter is preferably of the kind which in its opaque state has a very high optical density. Thus, the optical density high as 6 can be obtained, for example, by the use of an electro-optical shutter manufactured as a duplex structure comprising a pair of liquid crystal cells, in particular ferroelectric cells, with a common polarizer therebetween.

BRIEF DESCRIPTION OF THE DRAWINGS

For a better understanding of the present invention and to show how the same may be carried out in practice, reference will now be made to the accompanying drawings, in which.

DESCRIPTION OF THE PREFERRED EMBODIMENTS

Figure 1:
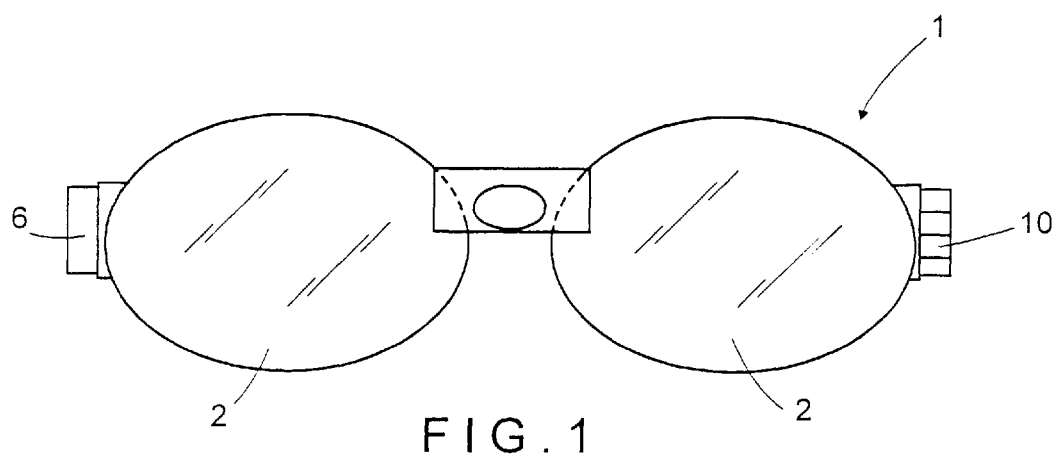
FIG. 1 is a front view of safety glasses according to the present invention.
Figure 2:
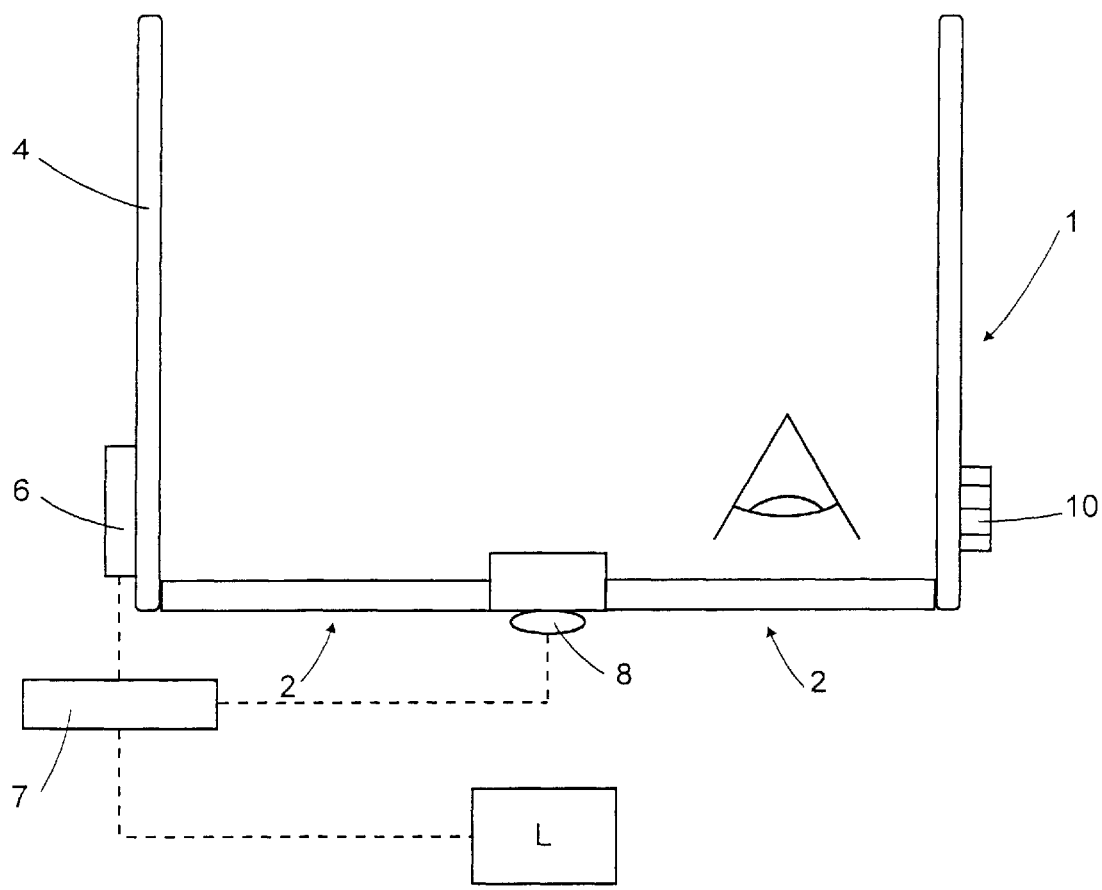
FIG. 2 is a top view of the safety glasses shown FIG. 1.

FIGS. 1 and 2 schematically illustrate safety glasses 1 for the protection of a user's eyes (only the left eye being shown) from a pulsed laser radiation of a laser L (shown schematically). The laser L has a delay time $\Delta t_d$ which passes between the laser triggering, internal or external, and the emission of each laser pulse.

Figure 3:
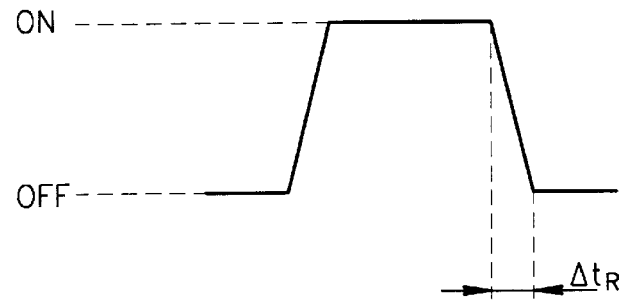
FIG. 3 illustrates a response curve of a liquid crystal shutter of the type used in safety glasses according to the present invention.

As shown, the safety glasses comprise a pair of lenses 2 and a frame 4 supporting the lenses. Each lens 2 is in the form of a liquid crystal shutter (LCS) capable of being switched by an electrical voltage signal from its transparent state (ON-state) to its opaque state (OFF-state). As illustrated in FIG. 3, the LCS has a response time $\Delta t_r$ which defines a time interval required for the LCS to be switched from its ON-state to its OFF-state.

As seen in FIG. 2, the safety glasses 1 further comprise power supply means 6 which supply voltage to the LCSs 2, thereby switching the latter to their opaque state, and control means 7 which are associated, on the one hand, with the power supply means 6 and, on the other hand, with the laser L to coordinate their operation.

The control means 7 can be connected with the power supply means 6 and the laser via electrical cables or rather, to avoid a physical connection between the user wearing the safety glasses and the laser, the latter can be provided with a remote IR transmitter (not shown) associated with a detector 8 attached to the glasses. Alternatively, the transmitter can be attached to the safety glasses and the detector to the laser, which allows for a more safe operation of the LCS. In this manner it is possible to ensure that the laser is triggered only after the control means verify that the LCSs are in their OFF-state and that if there is a problem in the glasses' operation (for example, weakening of the battery or disconnection), the operation of the laser will be interrupted immediately.

Figure 4:
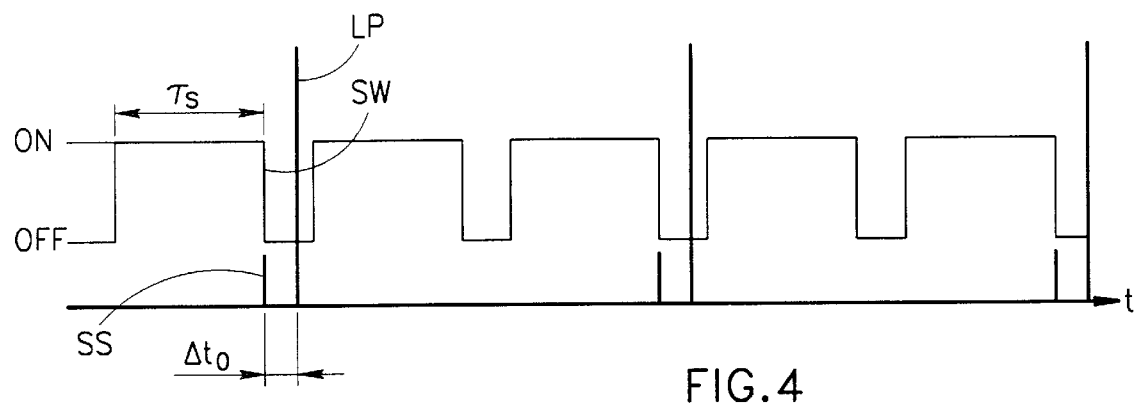
FIG. 4 illustrates a synchronization of operating regimes of a laser and of safety glasses according to the present invention, used in conjunction with the laser.

As illustrated in FIG. 4, in operation, an ON-OFF switch SW of the LCS activated by an appropriate electrical voltage signal supplied thereto by the power supply means 6, precedes the emission of each laser pulse LP by an operational time interval $\Delta t_o$ which is chosen so as to ensure that the switching of the LCSs into their OFF-state occurs always before the laser pulse LP is emitted. The LCS is kept closed at least until the laser pulse is emitted.

Thus, to provide effective protection, the operational time interval $\Delta t_o$ should by no means be shorter than the response time $\Delta t_r$ of the LCS. Therefore, for the device to be capable of fast operation, the LCS response time must be as short as possible. Thus, the LCS is preferably in the form of a ferroelectric liquid crystal having the response time of about a few tens microseconds. The advantage of using such a ferroelectric LCS is also that its response time $\Delta t_r$ can be shorter than the laser delay time $\Delta t_d$. This is particularly the case with various Q-switched lasers in which the internal delay time, i.e. the delay time between the laser triggering by a flash lamp signal or a diode current, is typically more than $100\mu$. In this case, the operational time $\Delta t_o$ can equal the delay time $\Delta t_d$ so that the LCS can be triggered simultaneously with the laser. Furthermore, the field of view of the ferroelectric LCSs is rather wide, i.e. about 130°.

To ensure effective protection, in addition to the appropriate choice of the operational time measures must be taken so that the operating regimes of the laser and the LCS are synchronized, ensuring that an LCS operating frequency $f_s$ is at least not lower than a triggering rate $f_l$ of the laser.

With reference to FIG. 4, the synchronization of phases of the LCS and the laser can be achieved by the provision of an initial synchronization signal SS sent from the laser to the LCSs or from the LCSs to the laser each time before triggering of the laser. Alternatively, in a case where the laser works at a constant rate or at small number of rates of pulse emission, the synchronization signal SS can be used only at the beginning of each operation.

To synchronize the operating frequency of the LCS $f_s$ with the triggering rate $f_l$ of the laser, it is generally suggested, in accordance with the present invention, that the operating frequency of the LCS satisfies the following relationship:

$$f_s = nf_l,$$

where n=1, 2, 3, etc.

It should, however, be borne in mind that it is extremely desirable that the effective protection provided by the safety glasses is combined with good vision therethrough when the changes from one state of the LCS to another are undetectable by the user. As indicated in U.S. Pat. No. 5,276,539 mentioned above, for the picture perceived by a user to be continuous, an operating frequency of the LCS must be not lower and preferably greater than a threshold frequency $f_o$ which is 20 Hz. It has been found by the authors that irrespective of the LCS operating frequency, the same result can be achieved if the time for which the user's field of view is blocked lasts not longer than a threshold time which is about 300 $\mu$s.

Applying the above conditions at which good vision can be achieved, to the above suggested relationship between the LCS operating frequency and the laser triggering rate, it can be concluded that the operating frequency of the LCS which equals the triggering rate of the laser (n=1) is suitable for the cases when the laser triggering rates are greater than the threshold frequency or when the available operational time interval of the safety device is shorter than the threshold time, irrespective of the laser triggering rate. When, however, the laser has low pulse repetition rates, the LCS operating frequency must equal a multiple of the laser triggering rate (n>1).

In a case where the laser has a range of different low triggering rates, the LCSs operating frequency can be chosen as a product of the laser pulse repetition rates.

To set up a desired operating frequency of the LCSs, the safety glasses can be provided with a selector knob 10 (FIG. 2) which can be controlled either manually or automatically, e.g. by the control means 7. Thus, the entire range of all possible frequencies of the LCS can be covered by several positions in the selector 10. For example, for a laser operating at a variable rate between 1 and 6 Hz, the corresponding frequency of the LCS will be 120 Hz, for a laser operating at a rate between 7 and 9 Hz, the LCS frequency will be 490 Hz and for a laser operating at a rate above 20 Hz, the LCS frequency will be double the laser operating rate. It is, however, clear that if the laser operates at a single rate or a small number of rates (as is commonly the case), the selector may be not needed at all.

An important advantage of the protection method and safety glasses according to the present invention is that they are suitable for any laser triggering rates, including a varying nonperiodic triggering rate. The maximal LCS switching frequency and, consequently, the maximal pulse repetition rate of the laser from which protection is possible are determined solely by the response time of the LCS. Thus, by using the ferroelectric liquid crystals as mentioned above, it is possible to achieve the LCS's switching rates as high as tens of kilohertz and to enable the method and the safety glasses according to the present invention to be used with a broad range of laser pulse repetition rates, from less than a few hertz to tens of kilohertz. In addition, the safety glasses using such LCSs are lightweight and not expensive.

Although the specific type of the LCS is chosen mainly according to its response time, there are two other very important parameters thereof which determine the quality of safety glasses and which therefore should be taken into consideration. These parameters are a mean transmittance T and a contrast ratio between the transmittance in the ON-state and in the OFF-state, the latter being defined by an optical density D of the LCS in these states.

The mean transmittance T through the LCS is given by the integral of the opening of the LCS per unit time over time. For operation at a constant operating frequency f and a transparency interval with a duration $\tau_s$ (FIG. 4), the mean transmittance of the light reaching the user's eyes through the LCS will be $T = \tau_s \cdot f \cdot T_{max}$, where $T_{max}$ is the transmittance of the LCS lens in its ON-state. It is clearly desirable that the mean transmittance is as high as possible in order to enable the user to work under poor illumination conditions. However, due to the decrease of the main transmittance caused by the components of the above relationship, the effective magnitude which can be achieved with LCSs based on polarization rotation is typically less than 40%.

The optical density in the OFF-state defines the level of protection provided by the safety glasses. This coefficient is determined primarily by the level of opaqueness of the LCS in its OFF-state, which depends on various parameters such as a radiation wavelength and ordering in the liquid crystal. With single-layer ferroelectric LCSs, the optical density greater than 3 can be achieved in the entire visible range.

Figure 5:
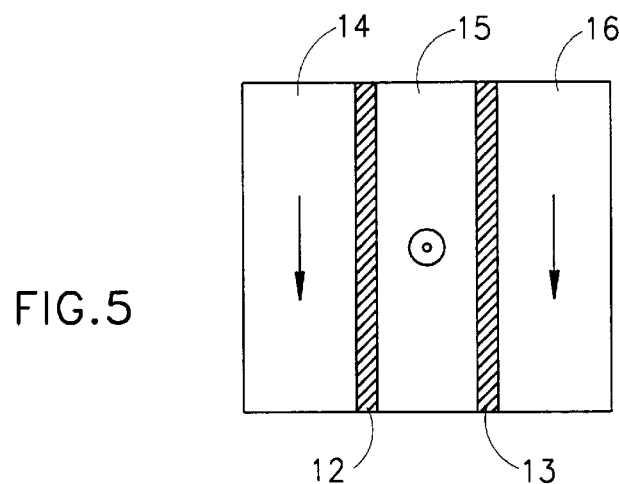
FIG. 5 is a schematic illustration of one embodiment of an LCS used in safety glasses according to the present invention.

If the above value of the optical density in the OFF-state is insufficient, which is very often the case in laser applications, a much better result can be obtained by a configuration of the LCS shown in FIG. 5. As seen, the LCS comprises a pair of LC cells 12 and 13 and three polarizers 14, 15, 16. In this configuration and with high quality polarizers being used, the optical density of the LCS in its OFF-state can reach 6. However, due to the use of the additional polarizer, the mean transmittance of the LCS is reduced.

If desired, it can be provided that before the laser is triggered, the optical density of the LCSs is verified to ensure that it has reached a required value. Thus, each LCS can be provided with a light emitting diode mounted on one side of the LCS and continuously emitting a detection light beam towards a photodetector mounted correspondingly on the other side of the LCS. When the electrical current provided by the photodetector drops below a certain value corresponding to the required optical density of the LCS, the trigger signal is passed to the laser.

It should be mentioned that, although the ferroelectric liquid crystals are preferred materials for protecting against pulsed laser radiation, any other suitable electro-optical shutters having a short response time and appropriate optical characteristics can be used.

It should also be understood that the present invention is not limited to the applications and features described in the specification and shown in the accompanying drawings.

I claim:

1. A method for the protection of a user's eye, or other radiation sensitive system, from a pulsed radiation emitted by a radiation source, by means of an electro-optical shutter used in conjunction with said radiation source and defining the field of view of the user or of the system, the electro-optical shutter being capable of being switched by an electrical voltage signal from a transparent state to an opaque state within a response time $\Delta t_r$; said method comprising:

applying said electrical voltage signal to said electro-optical shutter at an operational time interval $\Delta t_o$ prior to the emission of each radiation pulse, the operational time interval $\Delta t_o$ being at least slightly longer than the response time $\Delta t_r$ so that, by the time of emission of each radiation pulse, the electro-optical shutter is in its opaque state; and keeping said electro-optical shutter in its opaque state until the radiation pulse is emitted.

2. A method according to claim 1, wherein said electro-optical shutter is a liquid crystal shutter.

3. A method according to claim 2, wherein said liquid crystal shutter is of a ferroelectric type.

4. A method according to claim 1, wherein said radiation source is a pulsed laser which emits each radiation pulse within a delay time $\Delta t_r$ after the laser is triggered.

5. A method according to claim 4, wherein the response time $\Delta t_r$ of the electro-optical shutter is shorter than the delay time $\Delta t_d$ of the laser.

6. A method according to claim 5, wherein the operational time interval $\Delta t_o$ at least does not exceed the delay time $\Delta t_d$.

7. A method according to claim 4, further comprising synchronization of an operating frequency and exposure phase of the electro-optical shutter and a triggering rate and phase of the laser.

8. A method according to claim 7, wherein the condition for the synchronization of the operating frequency $f_s$ of the electro-optical shutter with the triggering rate $f_l$ of the laser is:

$$f_s = n f_l,$$

where n=1, 2, 3, etc.

9. A method according to claim 1, wherein an operating frequency of the electro-optical shutter is at least not lower than the recovery rate of the eye so that the picture perceived by the user is continuous.

10. A method according to claim 1, wherein the time for which the user's field of view is blocked lasts, irrespective of an operating frequency of the shutter, not longer than a threshold time detectable by the eye so that the picture perceived by the user is continuous with no flickering being seen.

11. A method according to claim 1, further comprising a fail safe operation which ensures that the radiation source is triggered only upon a verification of the fact that the electro-optical shutter is in its opaque state.

12. A method according to claim 1, further comprising a fail safe operation which provides for optical density detection of the electro-optical shutter, ensuring that the radiation source is triggered only after the optical density reaches its predetermined value.

13. A safety device for use in conjunction with a source of pulsed radiation having a predetermined pulse duration, for the protection of a user's eyes, or other radiation sensitive systems, from said pulsed radiation, the safety device comprising:

at least one lens defining the field of view of the user, the lens being in the form of an electro-optical shutter capable of being switched by an electrical voltage signal from a transparent state to an opaque state with a response time $\Delta t_r$ therebetween, said response time being longer than said pulse duration; and control means adapted for applying said electrical voltage signal to said electro-optical shutter an operational time interval $\Delta t_o$ prior to the emission of a radiation pulse, the operational time interval $\Delta t_o$ being at least slightly longer than the response time $\Delta t_r$ so that, by the time of emission of each radiation pulse, the electro-optical shutter is in its opaque state; and for keeping said electro-optical shutter in its opaque state until the radiation pulse is emitted, the time of said keeping the electro-optical shutter in its opaque state being not longer than a threshold time detectable by the eye.

14. A safety device according to claim 13, wherein the radiation source is a pulsed laser.

15. A safety device according to claim 13, wherein said electro-optical shutter is a ferroelectric liquid crystal shutter.

16. A safety device according to claim 15, wherein said electro-optical shutter is manufactured as a duplex structure comprising a pair of liquid crystal cells with a common polarizer therebetween, whereby an optical density of the electro-optical shutter is increased.

17. A system comprising a source of pulsed radiation having a predetermined pulse duration and a safety device for the protection of a user's eyes, or other radiation sensitive systems, from said pulsed radiation, the safety device comprising:

at least one lens defining the field of view of the user, the lens being in the form of an electro-optical shutter capable of being switched by an electrical voltage signal from a transparent state to an opaque state with a response time $\Delta t_r$ therebetween, said response time being longer than said pulse duration; and control means adapted for applying said electrical voltage signal to said electro-optical shutter an operational time interval $\Delta t_o$ prior to the emission of a radiation pulse, the operational time interval At being at least slightly longer than the response time $\Delta t_r$ so that, by the time of emission of each radiation pulse, the electro-optical shutter is in its opaque state; and for keeping said electro-optical shutter in its opaque state until the radiation pulse is emitted, the time of said keeping the electro-optical shutter in its opaque state being not longer than a threshold time detectable by the eye.

18. A system according to claim 17, wherein said electro-optical shutter is a liquid crystal shutter.

19. A system according to claim 18, wherein said liquid crystal shutter is of a ferroelectric type.

20. A system according to claim 17, wherein said radiation source is a pulsed laser which emits each radiation pulse within a delay time $\Delta t_d$ after the laser is triggered.

21. A system according to claim 20, wherein the response time $\Delta t_r$ of the electro-optical shutter is shorter than the delay time $\Delta t_d$ of the laser.

* * * * *